US00PP11347P

United States Patent [19]

van Geest

[11] Patent Number: Plant 11,347

[45] Date of Patent: Apr. 11, 2000

[54] FICUS PLANT NAMED 'WGN 56'

[75] Inventor: Jan van Geest, JP's-Gravenzande, Netherlands

[73] Assignee: Plantenkwekrij J. Van Geest B.V., JP's-Gravenzande, Netherlands

[21] Appl. No.: 09/086,315

[22] Filed: May 27, 1998

[51] Int. Cl.[7] ..... A01H 5/00

[52] U.S. Cl. ..... Plt./211

[58] Field of Search ..... Plt./211

[56] References Cited

U.S. PATENT DOCUMENTS

P.P. 9,856 4/1997 Van Geest ..... Plt./211

*Primary Examiner*—Howard J. Locker
*Assistant Examiner*—Wendy A Baker
*Attorney, Agent, or Firm*—Christie, Parker & Hale, LLP

[57] ABSTRACT

A variety of Ficus having dark green leaf blades with aristate leaf tip and semi-upright, weeping growth habit.

1 Drawing Sheet

BACKGROUND OF THE INVENTION

The present invention relates to a new and distinct cultivar discovered as a naturally occurring branch mutation in a controlled planting of *Ficus benjamina* 'Midnight' (U.S. Plant Pat. No. 9,856) in a greenhouse in The Netherlands. The varietal denomination of the new cultivar is 'WGN 56'.

SUMMARY OF THE INVENTION

'WGN 56' is a mutation of the variety *Ficus benjamina* 'Midnight'. The new variety has been asexually reproduced by rooted cuttings in The Netherlands. Asexual reproduction through succeeding generations has established that the combination of characteristics as herein disclosed for the new cultivar are firmly fixed and retained through successive generations of asexual reproduction. Various methods of asexual reproduction, such as micropropagation, layering and reproduction from vegetative cuttings, may be used to reproduce the new variety. 'WGN 56' has very dark green leaf blades that have undulating leaf margins with aristate leaf tip, and a semi-compact and semi-upright weeping growth habit.

COMPARISON WITH PARENT

The new cultivar differs from of the parent in leaf form and growth habit. The growth habit of the new cultivar, although upright, has a graceful cascading form due to the longer internodes. In addition, the leaf margins of the new variety are undulating and the leaf shape is ovate but somewhat elongated. It may be described as undulating, ovate-lanceolate with aristate leaf tip. This combination of characteristics gives the new variety a ruffled appearance.

BRIEF DESCRIPTION OF ILLUSTRATON

The accompanying illustration shows a specimen of the new cultivar in a photographic illustration as true to color as is reasonably possible to make in an illustration of this character. Phenotypical expression may vary depending on light, environmental and cultural conditions.

DESCRIPTION OF THE NEW VARIETY

The new variety is resistant to leaf drop under indoor lighting conditions and has sustained vigor for a period of 4 months indoors during the period of October to January in Homestead, Fla., under fluorescent lighting (averaging 200 fc).

In the description herein, color references are to The Royal Horticultural Society Colour Chart (R.H.S.C.C.). The terminology used in the color descriptions herein refers to plate numbers in this color chart.

The following description is from plants grown under a shade cloth greenhouse structure in Homestead, Fla., during the months of June 1997–January 1998; the shade cloth being about 83% shade cloth.

Habit:

*Form*.—The new variety is upward, vertically dominant, rather irregular and richly branching. Lateral branches are at about right angles to the trunk. They are straight initially, then weeping as they approach the apical tip.

*Growth*.—Vigorous growth habit with somewhat irregular branching.

*Height*.—The height attained to date is about 2 meters in 8 months from time of propagation and that height has been maintained by pruning.

Foliage:

*Size*.—About 75–82 mm in length×about 26–28 mm wide.

*Quantity*.—Numerous, multiple.

*Color*.—The color of the foliage is the same color as its parent. The leaves are extremely dark green. The young foliage emerges as a lighter green darkening to almost a blue-black green upon maturity. New foliage: Upper side near 141B; underside near 143A. Old foliage: Upper side near 131A; underside near 139A.

*Shape*.—Leaf shape is ovate lanceolate with a sharp aristate leaf tip.

*Texture*.—Leaf texture is smooth and glabrous and highly glossy.

*Veination*.—A single midrib vein runs from petiole to leaf tip, convex on the underside of the leaf, yellow green in color, near 145D.

*Edge*.—Leaf margins are wavy and undulating.

*Serration*.—None.

*Petiole*.—About 10–15 mm in length. Color: Top surface near 147B; undersurface near 147B.

Resistance to disease: Hardy as is its parent, though susceptible to *Agrobacterium tumefaciens* (Crown Gall). It is exceptionally resistant to leaf drop under low light conditions as are typical of interiorscape lighting (about 100–300 fc).

*Wood*.—Smooth. Color: New shoots are medium brown near 199A.

*Old wood*.—Color: Lightens to a creamy tan near 199D.

Winter hardiness: Can withstand cool temperatures to about 2° C., preferred growing temperature is about 25° C.–32° C.

Uniqueness: Foliage color, growth habit and low light tolerance when compared to *Ficus benjamina*, holds leaves better under interior light conditions; growth habit and appearance due to longer internodes; undulating leaf margins; irregular branching; and weeping habit.

Reproductive organs: None observed to date.

*Leaves*.—Texture: Smooth glabrous and glossy. Color: Dark green almost bluish-black. Form: Ovate-lanceolate with aristate leaf tip. Variegation: No variegation present. Veination: A single mid-rib vein running from petiole to leaf tip, convex on the underside of the leaf, and light yellow-green in color (near 145D).

*Plant*.—Temperature range: About 2° C.–40° C. Internode spacing: About 25–30 mm. Preferred growing conditions: About 25° C.–32° C. Growth habit: Irregularly branching upright with weeping apical branch tips.

I claim:

1. A new and distinct plant of *Ficus benjamina* substantially as illustrated and described.

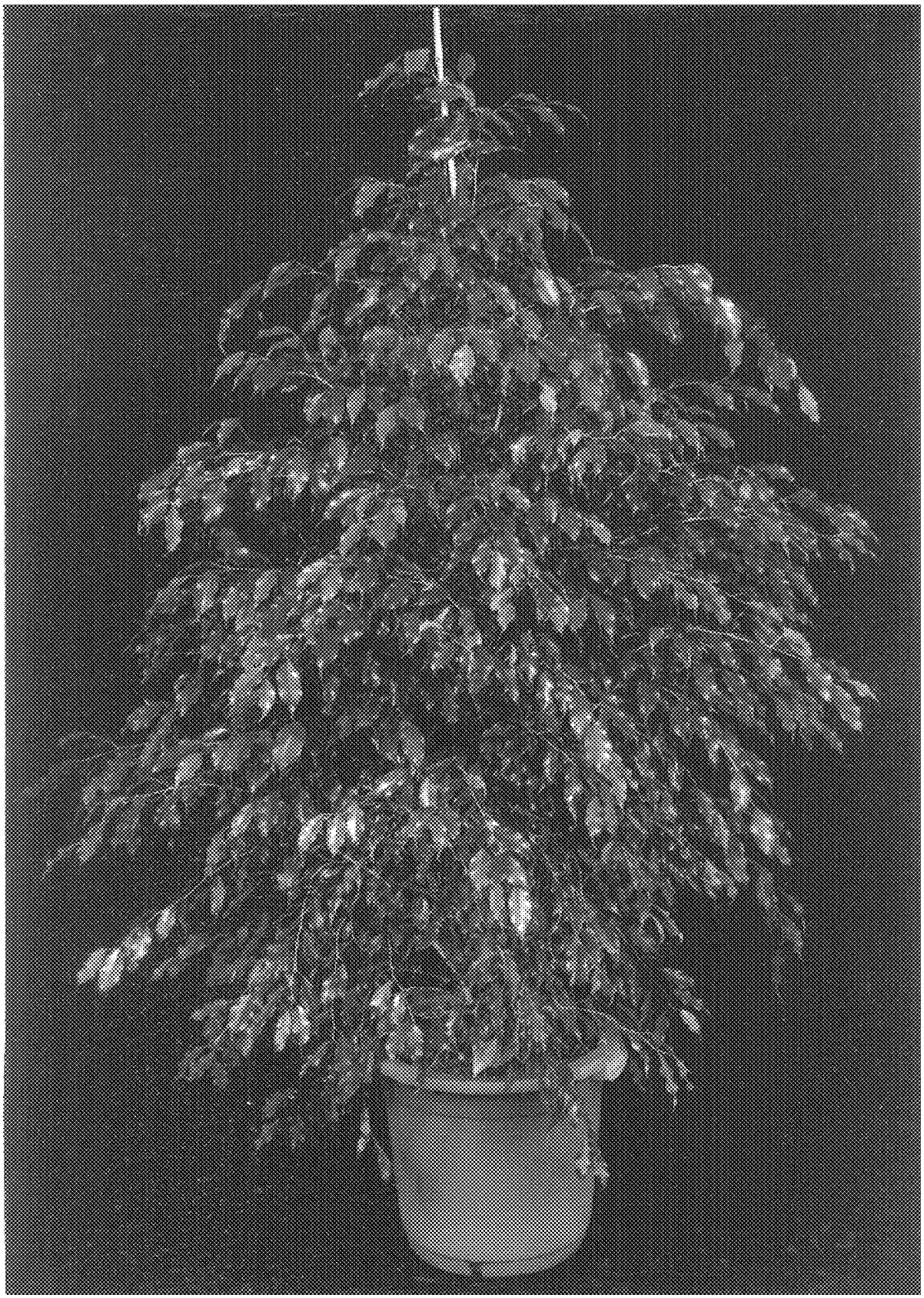

* * * * *